United States Patent
Booth et al.

(10) Patent No.: US 10,905,599 B2
(45) Date of Patent: Feb. 2, 2021

(54) ORAL HYGIENE SWAB

(71) Applicant: INTERSURGICAL AG, Vaduz (LI)

(72) Inventors: Christopher Edgerley Booth, Wokingham (GB); Matthew James William Leary, Wokingham (GB)

(73) Assignee: INTERSURGICAL AG, Vaduz (LI)

( * ) Notice: Subject to any disclaimer, the term of this patent is extended or adjusted under 35 U.S.C. 154(b) by 0 days.

(21) Appl. No.: 14/776,405

(22) PCT Filed: Jan. 20, 2014

(86) PCT No.: PCT/EP2014/051059
§ 371 (c)(1),
(2) Date: Sep. 14, 2015

(87) PCT Pub. No.: WO2014/139707
PCT Pub. Date: Sep. 18, 2014

(65) Prior Publication Data
US 2016/0038348 A1 Feb. 11, 2016

(30) Foreign Application Priority Data
Mar. 14, 2013 (GB) .................................. 1304610.7

(51) Int. Cl.
*A61F 13/38* (2006.01)
*A61C 17/02* (2006.01)
(Continued)

(52) U.S. Cl.
CPC ............ *A61F 13/385* (2013.01); *A46B 9/005* (2013.01); *A46B 15/0081* (2013.01);
(Continued)

(58) Field of Classification Search
CPC ..... A64B 9/005; A64B 15/0081; A61F 13/38; A61F 2013/4568; A61F 13/36–385;
(Continued)

(56) References Cited

U.S. PATENT DOCUMENTS 3,308,825 A * 3/1967 Cruse .................... A61M 1/008
27/24.2
3,373,492 A * 3/1968 Batch ................... A61C 17/043
433/91
(Continued)

FOREIGN PATENT DOCUMENTS

CN 202396799 U 8/2012
DE 3934227 C1 1/1991
(Continued)

OTHER PUBLICATIONS

International Preliminary Report on Patentability and Written Opinion of The International Searching Authority, for PCT/EP2014/051059, dated Sep. 15, 2015. Oct. 13, 2016.
(Continued)

*Primary Examiner* — Jacqueline T Johanas
*Assistant Examiner* — Shannel N Wright
(74) *Attorney, Agent, or Firm* — Troutman Pepper Hamilton Sanders LLP

(57) ABSTRACT

There is provided an oral hygiene swab (10) for a patient. The swab has a stem (12) formed of a first relatively rigid material and a head portion (14) formed of a second relatively softer material overmoulded onto the stem. The second material of the head portion is shaped to provide outwardly protruding cleaning formations (32, 36) for contact with the patient's mouth. The swab may be a suction swab and the stem may have a hollow interior.

26 Claims, 2 Drawing Sheets

(51) Int. Cl.
*A46B 9/00* (2006.01)
*A46B 15/00* (2006.01)
*A61F 13/00* (2006.01)
*A61F 13/15* (2006.01)
*A61F 13/45* (2006.01)

(52) U.S. Cl.
CPC ........ *A61F 13/00068* (2013.01); *A61F 13/38* (2013.01); *A46B 2200/1066* (2013.01); *A61C 17/0208* (2013.01); *A61F 2013/15154* (2013.01); *A61F 2013/4537* (2013.01); *A61F 2013/4568* (2013.01)

(58) Field of Classification Search
CPC ...... A61F 13/00085; A61F 2013/15154; A61F 2013/4537; A61C 17/0208; A61C 15/02; A61C 15/00; A61C 19/063; A61C 5/62; A61C 17/04–06; A46B 9/005; A46B 9/00–12; A46B 2200/1066; A46B 1/00; A46B 3/005; A61H 13/00; A61M 1/008; A61M 1/0082; A61M 1/0084
USPC ............... 433/91, 96; 601/141; 15/187, 188; 132/308, 313, 317, 321; 604/902; D24/108, 119
See application file for complete search history.

(56) References Cited

U.S. PATENT DOCUMENTS

| | | | |
|---|---|---|---|
| 3,516,410 A * | 6/1970 | Salomon | A61M 1/008 604/268 |
| 5,085,633 A | 2/1992 | Hanifl et al. | |
| 5,151,094 A * | 9/1992 | Hanifl | A61C 17/043 433/91 |
| 5,475,890 A | 12/1995 | Chen | |
| 5,704,785 A * | 1/1998 | Young | A61C 17/043 433/91 |
| 5,975,897 A * | 11/1999 | Propp | A61C 17/043 433/91 |
| 6,129,547 A * | 10/2000 | Cise | A61C 17/0208 433/80 |
| 6,238,213 B1 * | 5/2001 | Young | A61C 17/043 132/308 |
| 6,632,091 B1 | 10/2003 | Cise et al. | |
| 7,845,944 B2 | 12/2010 | DiGasbarro | |
| D660,599 S | 5/2012 | Hohlbein et al. | |
| 2003/0108846 A1 | 6/2003 | Hoertsch | |
| 2004/0087882 A1 | 5/2004 | Roberts et al. | |
| 2005/0069372 A1 * | 3/2005 | Hohlbein | A61B 17/244 401/132 |
| 2005/0149072 A1 * | 7/2005 | DeVries | A61B 1/32 606/153 |
| 2005/0166344 A1 | 8/2005 | Hohlbein et al. | |
| 2006/0010628 A1 | 1/2006 | Moskovich | |
| 2006/0195995 A1 | 9/2006 | Moskovich et al. | |
| 2006/0199147 A1 * | 9/2006 | Mahlmann | A61C 17/043 433/96 |
| 2007/0276326 A1 * | 11/2007 | DiGasbarro | A61C 17/043 604/131 |
| 2008/0147104 A1 | 6/2008 | Gatzemeyer et al. | |
| 2008/0300527 A1 * | 12/2008 | Bivins | A61F 11/006 604/1 |
| 2010/0240003 A1 * | 9/2010 | Fritze | A46B 9/005 433/80 |
| 2011/0151405 A1 * | 6/2011 | Dombrowski | A61C 17/043 433/96 |
| 2012/0045739 A1 * | 2/2012 | Schmidt | A46B 9/005 433/216 |
| 2014/0158152 A1 | 6/2014 | Butz et al. | |

FOREIGN PATENT DOCUMENTS

| | | | |
|---|---|---|---|
| DE | 19637689 A1 * | 5/1997 | ............ A61M 1/008 |
| DE | 102011011323 A1 | 8/2012 | |
| EP | 0447718 A1 | 9/1991 | |
| EP | 0993790 A2 | 4/2000 | |
| GB | 1060288 | 3/1967 | |
| GB | 2397525 A | 7/2004 | |
| WO | 2006055574 A2 | 5/2006 | |
| WO | 2006055574 A3 | 5/2006 | |

OTHER PUBLICATIONS

Search Report for Great Britain priority application No. GB1304610.7 dated Dec. 20, 2013.

International Search Report and Written Opinion for corresponding application No. PCT/EP2014/051059 dated Apr. 7, 2014.

Canadian Office Action for Corresponding Patent Application Serial No. 2,906,280, dated May 26, 2020.

\* cited by examiner

ORAL HYGIENE SWAB

This application is a national stage application under 35 U.S.C. § 371 of PCT International Application No. PCT/EP2014/051059, filed Jan. 20, 2014, which claims the benefit of Great Britain Application No. 1304610.7, filed Mar. 14, 2013, which are hereby incorporated by reference in their entirety.

This invention relates to oral hygiene products and, more specifically, to oral hygiene swabs for use in a medical facility, such as, for example, a hospital.

Intensive care hospital patients are often mechanically ventilated, and lie in a prone, unconscious position in bed. It is also common for such patients to be connected to a ventilator by an oral, nasal or tracheal connection. Patients are therefore unable to clean their own teeth, and usually lack the saliva which normally helps to remove bacteria and provide moisture to the mouth. Such a lack of oral hygiene is undesirable as it not only decreases the comfort of the patient, but also increases the risk of infection to the patient and others surrounding them.

The dental plaque of patients in intensive care sections of hospitals has been found to contain microorganisms that would not usually be present in the mouth. Examples of such microorganisms include *Klebsiella pneumonia, Pseudomonas aeruginosa* and *Staphylococcus aureus*, and these bacteria can cause severe infections, particularly if allowed to travel to the lungs. It is therefore necessary for medical practitioners or carers to maintain the oral hygiene of the patient and remove any bacteria from the mouth and oropharynx.

Known methods of maintaining oral hygiene involve the use of oral medical swabs. Aside from cleaning a patient's teeth alone, swabs are used for the cleaning of soft tissue and gums, for the suctioning of moisture, or for moistening the patient's mouth and/or lips. Swabs must accommodate patients having a full set, partial set or no teeth. Oral care swabs are commonly formed of a foam head, adhesively attached to a substantially straight plastic, stick-like handle and are usually manufactured at a very low cost.

There are numerous problems associated with the use of such swabs, one of the most commonly reported being that the foam head can become detached from the handle during use. This may be caused by the patient biting down on the swab and/or by the weakening of the adhesive during use. The foam head becoming detached in such a fashion poses a significant health risk to the patient, particularly if the head or debris is aspirated by the patient, since it may block the patient's air flow. This has the potential to cause severe harm to the patient, possibly even resulting in a fatality.

Furthermore it has been found that a conventional foam head can be abrasive to soft tissue within the mouth, particularly if the patient's carer uses a vigorous cleaning action and/or if the foam head is not fully laden with moisture. Thus conventional swaps have the potential of causing discomfort to the patient, especially if used to clean areas of inflammation.

It is an aim of the invention to provide a swab for which one or more of the above problems is at least partially mitigated.

According to a first aspect of the present invention there is provided an oral hygiene swab for a patient, the swab comprising a stem formed of a first relatively rigid material and a head portion formed of a second relatively softer material overmoulded onto said stem, wherein the second material of the head portion is shaped to provide outwardly protruding cleaning formations for contact with the patient's mouth.

The overmoulded nature of the head formation is beneficial in that it forms a bond between head and stem, ensuring adherence there-between even upon clamping forces on the head, caused by biting or the like. The overmoulding of the head portion creates a direct bond between the stem and head that is not reliant on an intermediate layer of adhesive and is thus not prone to problems caused by inconsistency of adhesive application or bonding.

It has also been found that the soft head portion material itself can be shaped to provide an effective cleaning action without the need for addition of a further material. This arrangement also provides a degree of protection to the patient, who may be unconscious, whereby the soft moulded head portion provides a cushioning resistance upon biting.

The head portion may be overmoulded over an end of the stem. The head portion may completely surround the end of the stem. The head portion may extend part way along the length of the stem.

The second material of the head portion may be substantially uniform or homogenous in structure. The second material may be of substantially constant density throughout its structure. That is to say the second material is typically not a cellular or foam material.

The second material may be a soft, malleable or pliable polymer. The second material may have a hardness of below 50 on the Shore A Scale and possibly a Shore A hardness of below 40 or 30. The second material may have a Shore A hardness of greater than 10, 15 or 20.

The second material may be a thermoplastic elastomer.

The second material may be hydrophobic, for example having a contact angle of 90° or greater upon contact with water. Alternatively, the second material may be hydrophilic.

The cleaning formations of the head portion may comprise a plurality of upstanding members. The upstanding members may depend outwardly from the stem in a substantially radial direction with respect to a longitudinal axis of the stem. The upstanding members may surround an end portion of the stem.

The head portion may comprise a plurality or series of upstanding walls, which may provide the cleaning formations. The walls may be upstanding with respect to the stem, for example with respect to a longitudinal axis of the stem. The walls may be substantially perpendicularly aligned with respect to the longitudinal axis of the stem.

The walls may be spaced. The walls may extend in a first direction (e.g. defining a width or lateral dimension of the walls) and may be spaced in a second direction, which is substantially perpendicular to the first direction. The second direction may be, or be substantially aligned with, the direction of the longitudinal axis of the stem.

The walls may be spaced by a short distance. The spacing between adjacent walls may be less than 3 mm or 2 mm and may be within the range 0.5-2 mm, for example approximately 1 mm.

The magnitude of the wall spacing may be of an order similar to the wall thickness. The wall thickness and spacing may be similar or approximately equal in dimension.

The provision of upstanding cleaning formations, such as walls, in close proximity is particularly beneficial since the head portion can be immersed in a cleaning liquid and, when removed therefrom, a volume of liquid will be retained between adjacent cleaning formations by capilliary action. When cleaning the mouth and oropharynx, contact between the soft cleaning formations and soft tissue or teeth causes deformation of the cleaning formations (i.e. relative movement between the walls), thereby overcoming the surface tension and any adherence between the liquid and the formations. This causes the liquid to be released during cleaning with a minimal contact pressure between the head portion and oral cavity.

The surface of the second material may be textured, thereby improving hydrophobic behaviour and/or cleaning action.

The walls may be curved in profile and may be generally circular, elliptical or annular in shape.

The walls may be arranged in a substantially linear array.

A first set of walls or formations may be spaced in a longitudinal direction relative to the stem axis. The second set of walls may provide a distal end or cleaning tip of the head portion. A second set of walls may oriented at an angle (i.e. non-parallel) to the first set, for example perpendicularly thereto. Additionally or alternatively the second set of walls may be spaced from the first set and/or may have differing dimensions to the first set of walls. In one embodiment, the second set of walls may extend substantially in the direction of the longitudinal axis and may be spaced laterally or radially relative thereto. In different embodiments, the cleaning head may comprise either or both of the first and/or second sets of walls.

The head portion may be curved in profile and may be a body of revolution. The outer periphery of head portion may be circular or elliptical in section (e.g. in cross section). The outer periphery of the head portion may be at least partially curved in longitudinal section. The head may be generally ellipsoid, globoid, ovoid, cylindrical, conical or frusto-conical in shape and may be shaped in the manner of a bud, lozenge or other body of revolution.

The stem and/or head portion may have a hollow interior. The stem may define a longitudinal internal passage along its length, which may be in communication with the head portion. The head may define openings to the internal passage. The openings may be provided between the cleaning formations. The openings may allows communication between the internal passage and the exterior of the head portion.

The swab may be a suction swab.

The stem may have a connector formation spaced from the head portion. The connector may be a fluid flow connector allowing fluid communication with the head. The connector allows a negative pressure or suction force to be applied to the head openings via the internal passageway. The connector may be provided at a proximal end of the stem.

The stem may comprise a handle portion and a neck portion. The neck portion may be interposed between the handle portion and the head portion. The handle may be rigidly or releasably connected to the neck portion. The handle and neck may be connected by a snap-fit connection. The handle may be received within the neck portion. The connector may be provided on the handle, e.g. at a proximal end thereof.

The handle portion may comprise one or more grip formations.

The stem may have an opening or window part-way along its length (e.g. provided in the handle or neck portion thereof). The opening may comprise a port provided in an outer or side wall portion of the stem, which may provide an opening into the internal passage within the stem. The opening may be provided in the handle portion of the stem such that it is accessible by a thumb of a user whilst gripping the stem with one hand.

According to a second aspect of the present invention, there is provided a method of manufacture of an oral hygiene swab, the method comprising moulding a stem of a first relatively rigid material, overmoulding a head portion of a second relatively softer material onto said stem, wherein the mould for the second material is shaped to define cleaning formations in the head portion formed of said second material.

The stem and/or head may be injection moulded. The first and/or second materials may be polymers. The stem and head may be entirely formed of said first and second materials.

The stem may be formed as separate handle and neck components, which may have corresponding connector formations thereon.

Any of the optional features defined in relation to the first aspect may be applied to the second aspect and vice versa.

Practicable embodiments of the invention are described in further detail below by way of example only with reference to the accompanying drawings, of which:

FIGS. 4A-H show various examples of different embodiments for the head portion of a swab according to the invention.

Figure 1:
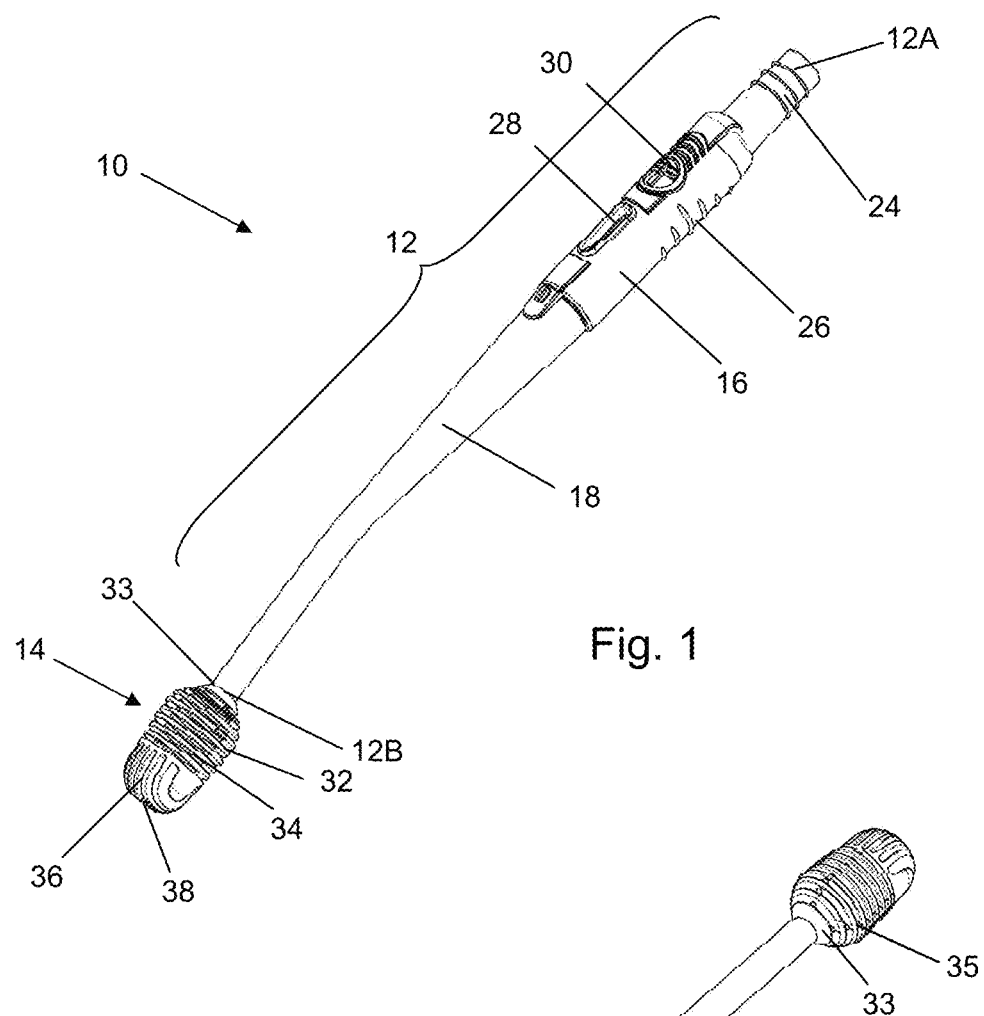
FIG. 1 shows a three-dimensional view of a swab according to an example of the invention from a distal end thereof.
Figure 2:
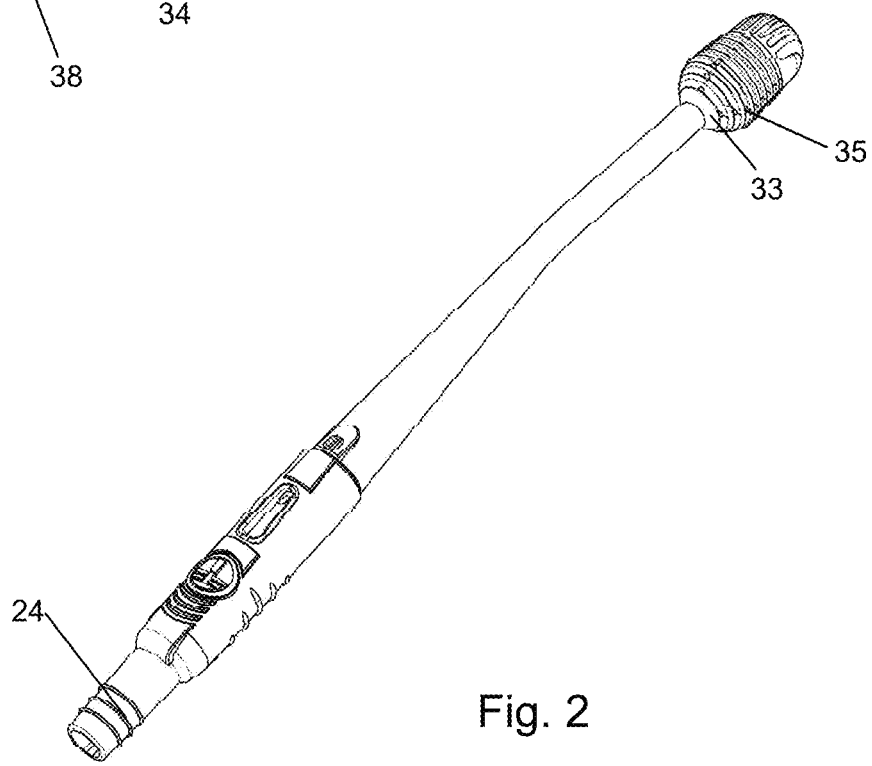
FIG. 2 shows a three-dimensional view of the swab of FIG. 1 from a proximal end.
Figure 3:
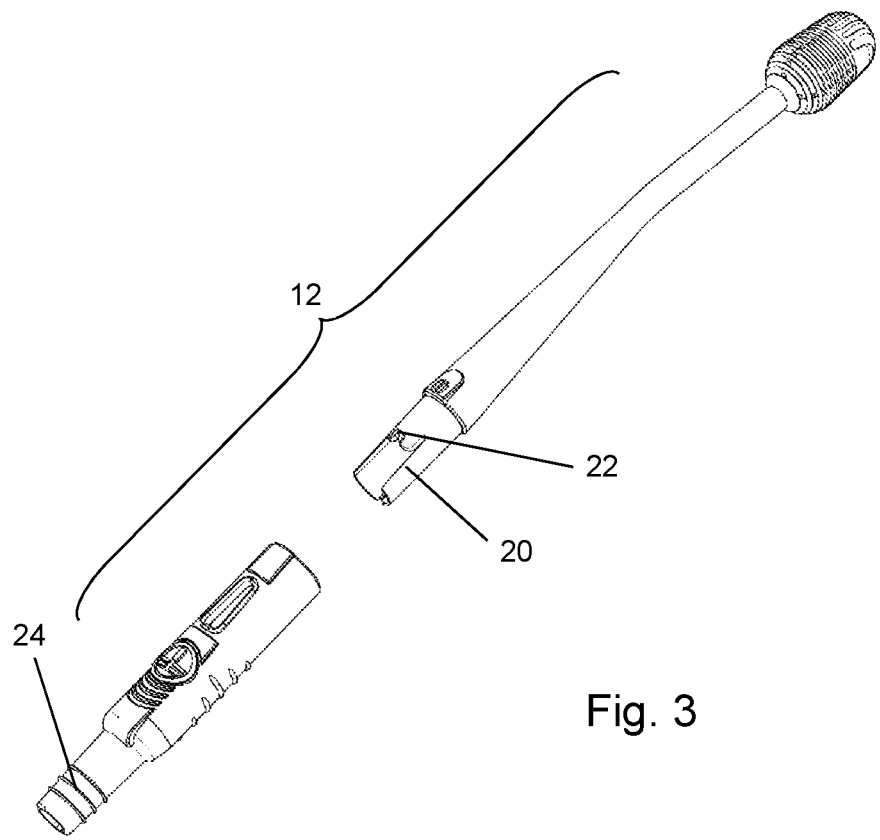
FIG. 3 shows an exploded three-dimensional view of the swab of FIG. 1.

With reference to FIGS. 1 to 3, there is shown an oral hygiene/cleaning device in the form of a swab 10 intended for use by a carer, such as a medical professional, for cleaning the oral cavity and/or oropharynx of a patient. Such swabs have been developed in order to allow a gentle cleaning action by a carer, rather than by a patient him/herself, given the different states of consciousness or physical ability to which a patient may be subjected. Such gentle cleaning has been found to be important particularly if insufficient saliva is present within the mouth.

The swab 10 is intended to be a single-use or disposable article.

The swab 10 in this embodiment is a so-called suction swab.

The swab 10 comprises an elongate stem 12 having a proximal end 12A and a distal end 12B. A head formation 14 is provided on the stem 12 at the distal end 12B thereof. The head 14 is affixed to the stem 12 in a manner such that the head and stem form a single article. The head cannot be removed from the stem without permanent deformation or breaking of the article.

The stem is formed of a rigid mouldable polymer material, for example a thermoplastic, such as polypropylene, although it will be appreciated that similar alternative conventional plastic materials may be used. The stem has a hollow interior allowing fluid communication along the length of the stem between its proximal 12A and distal 12B ends. The hollow interior of the stem defines an elongate internal fluid passage running the entire length of the stem.

The stem is generally tubular in shape but has a taper such that the stem narrows towards it distal end 12B in proximity of the head 14. The stem 12 is wider towards proximal end 12A, thereby defining a handle or grip portion, spaced from the head by an intermediate section of the stem. The handle or grip portion is thus more comfortable to hold securely by a user than the narrower, intermediate portion of the stem.

Turning to FIG. 3, it can be seen that the stem 12 is formed of two parts, namely the handle 16 and the neck 18. The head 14 is permanently affixed to the neck 18 at the distal end thereof. Thus the neck 18 provides the intermediate portion of the stem between the handle 16 and the head 14. The neck 18 is angled slightly, e.g. typically between 1° and 5°. This may help to improve viewing angle and/or cleaning action in use.

The neck 18 and handle 16 are attached by a push-fit type connection. As shown in FIG. 3 the neck 18 has a male connector end 20 which is insertable into the open end, or female connector portion, of the handle 16. The connector end 20 has a lip 22 or other retaining formation which engages a corresponding opposing formation (not shown) within the handle 16 so as to securely fasten the two components together. Such a push-fit or snap-fit connection is generally not intended to be reversible such that the swab 10 as a whole is disposable after use. However in other embodiments alternative connection arrangements may be provided, such as a screw thread or bayonet fitment. In some embodiments, the handle and neck may be disconnectable such that, for example, the neck and head may be disposed of, whereas the handle may be retained for further use. Thus a plurality of neck parts, potentially of differing types, may be interchangeable on a common handle.

The connector end 20 may also have an alignment formation such that the neck 18 and handle 16 are only connectable when those two parts are correctly rotationally aligned. This may be achieved by the locations of the retaining formation on the connector end and the opposing formation on the interior of the handle or else by provision of a protrusion-and-recess (e.g. slot) alignment arrangement or similar.

Whilst the neck 18 is described as having the male connector formation in this embodiment, it will be appreciated that the male and female arrangement of the connector may be reversed if necessary.

The neck and handle portions of the stem fit closely together so as to form an effective seal there-between. The seal is typically water-tight and may also be generally gas-tight, at least under relatively low, conventional suction pressures.

The handle 16 comprises a connector formation 24 at its proximal end (i.e. end 12A of the stem) for connection to conventional tubing. This allows fluid connection to conventional suction-inducing apparatus in use as would be understood by the person skilled in the art.

The handle 16 has one or more grip formations 26 such as ridges or the like, which may serve to indicate the location at which the device is intended to be held and also to reduce the likelihood of the handle slipping in the hand of the user.

Whilst the handle 16 and neck 18 are described above as two components joined together, it is possible that in other embodiments, they may be formed as a single member, for example by forming the elongate neck as a simple, generally tubular member and overmoulding a grip portion thereon.

The stem 12 is bowed or otherwise curved or kinked slightly, typically in the vicinity of the neck 18. Thus the handle portion 16 is angularly offset slightly from the end 12B of the neck, typically by between 1° and 5°, although larger angles may be preferable.

An opening 28 is provided in the handle portion 16 adjacent the region intended to be gripped by a user. The opening 28 is elongate or oblong in form but may be round, elliptical or trapezoidal if desired. The opening 28 provides a port that can be selectively open or else covered by a user's thumb. Thus the opening is typically located on an upper side of the handle as may be indicated by one or more indicia, such as a logo 30, which may be formed adjacent the opening 28 by the moulding process.

The head 14 is formed of a softer moulded material, such as a thermoplastic elastomer. The hardness of the softer material may be customised dependent on the cleaning requirements of the swab. A shore A hardness range of 1-50 may be used. In some embodiments it is expected that a Shore A hardness of 10-40 would be suitable. In the present example, a Shore A hardness of 20-35 has been found to be effective. However a Shore A hardness of less than 30 or 20 may be desirable in other embodiments for cleaning particularly sensitive soft tissue regions.

Examples of suitable materials for the softer moulded material comprise, typically hydrated, styrene block copolymers such as Thermolsat K®, Evoprene®, Dryflex®, or Mediprene®, although other conventional polymer materials may be used provided they display the necessary malleability characteristics.

The head 14 is formed on the end portion 12B of stem 12 by over-moulding. This may be achieved by a two-shot moulding process within one mould (i.e. by first injecting the stem material at an elevated temperature and subsequently injecting the material of the head 14 onto the stem material as it is hardening). A multi-cavity mould may be provided to define the different material portions. Alternatively, stems 12 (or necks 18) may be formed in a first mould and transferred to a second mould in which the mould cavity is shaped to define the head 14 around the existing stem. Conventional injection moulding delivery systems may be used to control the temperature and pressure of the polymer materials such that they enter the mould cavity in the desired liquid state.

The overmoulding of the head in the above-described manner means that the material of the head portion 14 is brought into contact with the neck 18 whilst in a liquid state and thereby wets the end portion of the neck. The material of the head portion is maintained in contact with the neck whilst cooling so as to solidify in contact therewith, thereby ensuring that a consistent and permanent bond is formed directly between the two materials.

The head 14 is shaped in a bespoke manner to provide a suitable cleaning formation for contact with a patient's oral cavity. In particular the head has a hollow interior, thereby forming an internal passage (not shown) which is in communication with the internal passage of the stem 12. In this example, the internal passage of the head 14 is an extension of the internal passage of the neck 18 and extends in the direction of the longitudinal axis of the neck 18.

The head comprises a first set of annular walls or rings 32 formed about the internal passage. The annular walls are substantially aligned with the longitudinal axis of the neck such that said axis is also substantially at the centre of the annular walls. The annular walls 32 are spaced along the axis by a short distance, which is in this example between 0.5 and 1.5 mm, such as approximately 1 mm. The annular walls may themselves each be 1 mm or less in thickness.

A total of six to eight walls 32 are provided in this embodiment. In other embodiments, it is envisaged that anywhere between four and fifteen such walls could be provided.

A thicker end portion or wedge 33 (see FIG. 2) may be provided at the end of the head 14 that connects to the neck. This may help increase the strength of the head and the connection with the stem.

A plurality of ridges or supports 35 are provided which span the adjacent annular walls 32. The supports 35 extend in the direction of the longitudinal axis and serve to hold adjacent annular walls at the required spacing as well as improve the structural strength of the head. In this example four supports are provided at equal spacing about the longitudinal axis (i.e. at 90° spacings) although in other examples, it is envisaged that three or more supports may be suitable.

The spacing of the annular walls 32 provides a series of radial passages 34 between adjacent annular walls 32 which communicate between the exterior of the head and the internal passage. Thus the end 12A of the stem is in fluid communication with the exterior of the head via said openings. The passages 34 are generally annular in shape and terminate at circumferential/peripheral openings about the external surface of the head. In the example shown the supports intersects each annular passage such that the annular passage is split into a corresponding plurality of generally wedge shaped passage portions which in combination approximate the complete annulus.

The series annular walls 32 defines a major part of the head 14, specifically the portion of the head proximate the end 12B of the stem. The free/distal end of the head 16 has a further series of spaced walls 36. The dimensions and spacing of those walls 36 may be similar to those of walls 32 described above. However, in this embodiment, the walls 36 are preferably of slightly greater thickness (e.g. 1 mm or greater in thickness) and spacing. The added thickness increases the rigidity of the walls 36 in light of their intended function to be described below.

The walls 36 are arranged as a series of end walls defining a cleaning structure at the tip of the head. The end walls 36 share a common base, which is formed as the final annular wall 32 of the first series. The end walls 36 are upstanding from that base such that the walls depend therefrom in a direction substantially aligned with the longitudinal axis of the stem. The edges of the end walls are curved or arcuate in plan and the walls may be approximately semi-circular, semi-elliptical or semi-ovoid in shape.

Although described herein as being perpendicularly arranged, the walls 32 of the first series may otherwise be obliquely angled relative to the walls 36 of the second series. For example, either set of walls may lean in a forward or backward slant, or either of said sets of wall may be doubly angled, for example in a herringbone pattern or similar.

One or more of the walls 36 towards the middle of the series (i.e. close to the longitudinal axis) may have a central cut-out 38. Thus the cut-out 38 may provide an open end of the internal passageway such that the passageway passes right through the head 14 (i.e. the entire length of the swab). In this manner, the second series of walls 36 provides an opening in the longitudinal, rather than radial direction.

In use, the swab is connected to conventional vacuum equipment at connector end 24, typically via in intermediate hose. The connector 24 accommodates standard suction lines.

The opening 28 allows the user to select whether the negative suction pressure is applied to the head 14. In the event that the opening is uncovered, the applied suction will draw ambient air in to the opening 28, thereby short circuiting the head. Selectively covering the opening 28 by the user's thumb allows the suction pressure to be experienced at the head 14, thereby drawing any liquid and debris in the vicinity of the head through the openings in the head and along the neck 18.

The user can submerge the head 14 into a liquid suitable for cleaning the oral cavity. Any conventional oral cleaning solution and/or suspension may be used which may comprise antiseptic or conventional mouthwash, which could, for example, contain chlorhexidine. The spaced wall configuration of the head causes liquid to be drawn in-between the adjacent walls by capillary action (i.e. due to the surface tension of the liquid) regardless of whether suction is applied. When the head is removed from the liquid, the volume of liquid between the walls remains trapped and can be conveyed to the patient's mouth.

The user can rub the cleaning head 14 against the teeth and soft tissue within the mouth and oropharynx, whereby contact with the cleaning head deforms the malleable walls and thereby releases the cleaning liquid. The liquid can thus be moved around the patient's oral cavity in a brushing motion. The end walls 36 allow the brush to be used end on, whilst the annular walls allow for a lateral brushing action such that any movement against the patient's oral cavity will produce some form of cleaning action regardless of brush orientation. Also, the head arrangement described above allows more precise cleaning of regions, particularly in the vicinity of a patient's teeth, than a conventional foam head.

With the cleaning head inside the patient's oral cavity, the user may cover the opening 28 to selectively apply suction to the cleaning head so as to remove excess cleaning liquid, mucus/saliva, other secretions or debris from the patient's mouth.

The secure bond between the head and neck ensures that the head does not become detached even in the event that the patient bites on the head. The improved bond interface between the head and stem can thus be readily discerned by the skilled person when compared to the provision of a separate adhesive material for fixation of the head.

It has been found that the soft pliable TPE material may be hydrophobic and, when moistened, can improve capillary action and thereby ensure an adequate volume of cleaning fluid is drawn into the head to be dispensed during cleaning. Further analysis of this feature has revealed that either hydrophobic or hydrophilic surface qualities can be provided for different reasons. For example, a hydrophilic surface can better retain liquid at its surface to avoid an abrasive effect on tender oral tissue due to the head drying out. A suitable surface texture or treatment may be applied to achieve any such aims. In either embodiment, it has been found that the head portion of the present invention can provide a less abrasive cleaning action than many conventional foam swab materials.

After use, the swab 10 may be detached from the suction hose and disposed of as a single article.

FIGS. 4A-4H, there are shown a number of different arrangements/geometries of the cleaning head that can be used to replace the head portion 14 of FIGS. 1-3. Any of the foregoing description of the swab 10 may apply to the embodiments of FIGS. 4A-4H, except for the differences described below. The embodiments of FIGS. 4A-4H are provided as examples of design changes, any or any combination of which may be applied to the head portion of the swab without necessarily requiring the relevant alternative head portion need be adopted in its entirety.

Figures 4A, 4B, 4C, 4D:
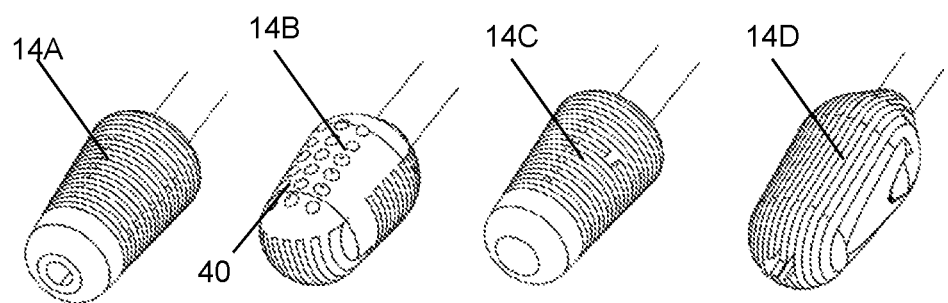

In FIGS. 4A, 4C, and 4D, it can be seen that a single set of wall formations may be provided in cleaning heads 14A, 14C, and 14D, respectively. In such embodiments, the distal end of the cleaning head may comprise a tip formation of greater wall thickness than the individual walls so as to provide an end stop formation of increased resilience. The internal passage of the head portion may extend through the distal end as shown in FIGS. 4A and 4E (i.e., head portions 14A and 14E, respectively) or else may be closed off by the end stop as shown in FIG. 4C (i.e., head portion 14C).

In FIG. 4D, there is shown an arrangement in which longitudinally aligned cleaning walls may be provided over substantially the whole length of the cleaning head 14D in place of the laterally extending walls of the other embodiments. In FIG. 4F, a tip region 14F is formed of walls having reduced and/or diminishing radial dimension compared to the walls in the remainder of the head portion. In this example, the walls in the tip region may be substantially parallel with the remaining walls.

Figures 4E, 4F, 4G, 4H:
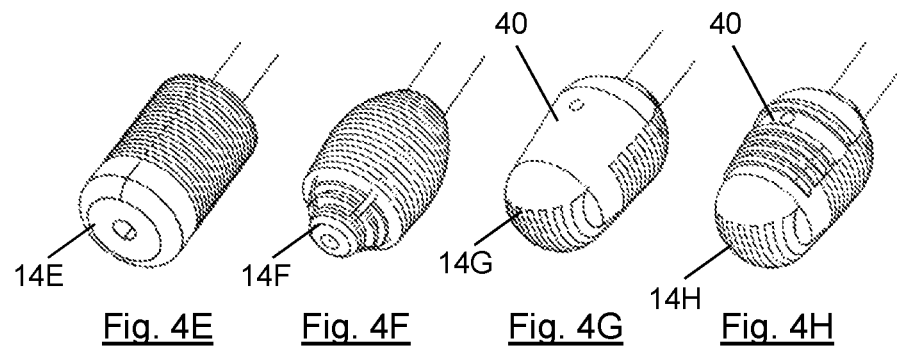

In FIGS. 4B, 4G, and 4H cleaning heads 14B, 14G, and 14H, respectively, has have two sections comprising a first section having the cleaning walls of any of the embodiments described above and a further section, labeled 40. The further section 40 may comprise a base section from which the walls depend. For example the base may extend in a longitudinal, rather than axial direction and may form at least a portion of the outer periphery of the head portion. The base may form a minor portion of the periphery of the cleaning head. In the example of a cleaning head that is circular in section, the base may form a circular segment in section.

The base 40 may be used to improve the resilience or strength of the cleaning head. Additionally or alternatively, the base 40 may be used to provide a support for one or more additional cleaning formations, which may be of a different type to the walls 34 or 36 described above. The additional cleaning formations may comprise, for example, a plurality of raised nodes as shown in FIG. 4B (14B) or else a plurality of ridges as shown in FIG. 4H (14H). Those formations may serve as massaging formations and may be of greater resilience than the relatively thin walls described above. The embodiment of FIG. 4H (14H) may provide material removal formations, for example in the manner of a so-called tongue scraper.

The invention claimed is:

1. An oral hygiene swab for a patient, the swab having:
   a stem comprising a handle portion and a neck portion, the stem comprising a first rigid material;
   a head portion comprising a second material overmoulded onto said stem such that there is a direct bond between the stem and the head portion with no intermediate layer of adhesive, wherein the second material is relatively softer than the first rigid material; and
   cleaning formations on the head portion for contact with the patient's mouth, the cleaning formations comprising a plurality of discrete annular walls, the plurality of discrete annular walls aligned with a longitudinal axis of the neck portion such that the axis is substantially at the center of the annular walls, wherein the plurality of discrete annular walls define a series of discrete radial passages, each of the discrete radial passages located between adjacent annular walls, wherein a plurality of supports are provided spanning the plurality of annular walls, and
   wherein the second material of the head portion is shaped to provide the cleaning formations,
   wherein the stem and head portion have a hollow interior, thereby defining an internal passage along the swab, and
   wherein the head portion has a plurality of openings in communication between the internal passage and the discrete radial passages of the swab, the openings being arranged between the cleaning formations.

2. An oral hygiene swab according to claim 1, wherein the head portion surrounds an end of the stem and is shaped to provide the cleaning formations, the cleaning formations depending outwardly from the head portion.

3. An oral hygiene swab according to claim 1, wherein the second material is a thermoplastic elastomer.

4. An oral hygiene swab according to claim 1, wherein the second material has a hydrophobic or hydrophilic surface.

5. An oral hygiene swab according to claim 1, wherein the annular walls are upstanding with respect to the longitudinal axis of the stem.

6. An oral hygiene swab according to claim 5, wherein the annular walls extend in a circumferential direction about the longitudinal axis of the stem.

7. An oral hygiene swab according to claim 5, wherein the annular walls are arranged in an adjacent manner in series with close spacing between each adjacent annular wall.

8. An oral hygiene swab according to claim 5, wherein the annular wall thickness and/or spacing between each annular wall is less than 2 mm.

9. An oral hygiene swab according to claim 7, wherein the annular walls are arranged to retain liquid between each adjacent annular wall in use under capillary action at ambient or undisturbed conditions.

10. An oral hygiene swab according to claim 5, wherein the annular walls are circular.

11. An oral hygiene swab according to claim 5, wherein the head portion comprises a further set of cleaning formations.

12. An oral hygiene swab according to claim 11, wherein the further set of cleaning formations are arranged at a distal end of the head portion.

13. An oral hygiene swab according to claim 11, wherein the further set of cleaning formations comprise a further plurality of walls, said further walls being generally aligned in parallel and angularly offset from the first set of cleaning formations.

14. An oral hygiene swab according to claim 1, wherein the head portion comprises a base from which the cleaning formations depend, the base comprising the second material and forming a portion of the exterior of the head portion.

15. An oral hygiene swab according to claim 14, wherein an additional set of cleaning formations is provided on the base.

16. An oral hygiene swab according to claim 5, wherein a spacing between the annular walls defines the openings into the hollow interior of the head portion.

17. An oral hygiene swab according to claim 1, comprising a suction swab, wherein the stem has a connector formation spaced from the head portion, the connector allowing fluid communication between a suctioning equipment and the head portion.

18. An oral hygiene swab according to claim 17, wherein the stem has a port therein to allow selective application of suction to the head portion by opening or covering the port.

19. An oral hygiene swab according to claim 1, wherein the handle portion and neck portion are connectable such that the handle portion is spaced from the head portion by the neck portion.

20. An oral hygiene swab according to claim 19, wherein the handle and neck portions are connected by a snap-fit connection.

21. An oral hygiene swab according to claim 1, wherein the second material has a Shore A hardness of below 50.

22. The oral hygiene swab according to claim 1, wherein the head portion comprises a cut-out in the end of the head portion, the cut out providing an open end of the internal passage along the swab.

23. The oral hygiene swab of claim 1, wherein the plurality of supports extend in a direction of the longitudinal axis of the neck portion.

24. The oral hygiene swab of claim 23, wherein the plurality of supports comprises four supports provided at 90° spacings aligned with the longitudinal axis of the neck portion.

25. The oral hygiene swab of claim 23, wherein the plurality of supports intersect each passage such that the passages are split into a plurality of wedge-shaped passage portions.

26. The oral hygiene swab of claim 1, wherein the plurality of supports is a plurality of support ridges spanning the plurality of annular walls and serving to hold adjacent annular walls at a required spacing.

* * * * *